United States Patent [19]

Swanson

[11] 4,164,793
[45] Aug. 21, 1979

[54] LUNATE IMPLANT

[76] Inventor: Alfred B. Swanson, 2945 Bonnell, S.E., Grand Rapids, Mich. 49506

[21] Appl. No.: 900,188

[22] Filed: Apr. 26, 1978

[51] Int. Cl.² .............................................. A61F 1/24
[52] U.S. Cl. .................................... 3/1.91; 128/92 C
[58] Field of Search .............................. 3/1.9, 1.91, 1; 128/92 C

[56] References Cited

PUBLICATIONS

"Silicone Rubber Implants for Replacement of Arthritic or Destroyed Joints in the Hand", by Alfred B. Swanson, Surgical Clinics of North America, vol. 48, No. 5, Oct. 1968, pp. 1113-1127.

"Flexible Implant Resection Arthroplasty in the Hand and Extremities," (Book) by Alfred B. Swanson, The C. V. Mosby Company, Saint Louis, 1973, pp. 1-6, 15, 16, 30, 31 & 242-253.

Primary Examiner—Ronald L. Frinks
Attorney, Agent, or Firm—Price, Heneveld, Huizenga & Cooper

[57] ABSTRACT

A flexible implant for replacement of the lunate bone of the wrist includes a one-piece body of resilient material defining a planar triquetrum face having a general U-shape in plan and further including a stabilizing stem extending outwardly from and perpendicular to the planar triquetrum face and a planar scaphoid face having a generally U-shape in plan extending at an angle with respect to the triquetrum face. The body further includes a cupped, concave, smooth distal surface adapted to articulate with the head of the capitate bone. The body defines a proximal surface having a smooth convex shape and extending between the proximal edges of the triquetrum and scaphoid faces. Generally planar palmar and dorsal surfaces extend between the dorsal lateral edges and the palmar lateral edges of the triquetrum and scaphoid faces.

7 Claims, 10 Drawing Figures

LUNATE IMPLANT

BACKGROUND OF THE INVENTION

The present invention relates to arthroplastic reconstruction of the human joints and more particularly to flexible implant resection arthroplasty of the wrist joint.

In recent years, silicone implants have been successfully employed for the restoration of function of the joints of the hand affected with rheumatoid arthritis and similar conditions. The procedures developed have generally been found to be more successful than prior attempts to restore motion by soft tissue arthroplasties and by the use of metal implants. Due to the shortcomings of prior conventional operational procedures to correct deformities of the wrist joint, flexible implants for this specific joint were developed. Proper function of the wrist joint is necessary for proper function of the hand. A stable and mobile joint is necessary for the proper transmission of muscle forces and for the normal moving and grasping of objects by the hand encountered in normal activities.

Aseptic necrosis and/or arthritis of the carpal bones, either primary or secondary to trauma, is a frequent cause of disability of the wrist joint. Surgical treatment of conditions of the wrist joint have included intercarpal fusion, wrist fusion, local resection, proximal row carpectomy, bone grafting, radial styloidectomy, radial shortening or ulnar lengthening, and soft tissue interposition arthroplasty. Fusion procedures do not provide optimum results since the stability, power and mobility of the wrist is affected even though pain is relieved. Local resection procedures, which involve the removal of an irreversibly pathological bone, are complicated by migration of adjacent carpal bones in the space left by the resection. This results in instability in the wrist joint. Metallic and acrylic implants for the replacement of carpal bones were not satisfactory due to problems relating to progression of the arthritic process, migration of the implant, breakdown of the material and absorption of bone due to hardness of the material inserted.

As a result of the shortcomings of such operative procedures, intramedullary stem silicone rubber implants were developed to replace the lunate bone of the carpal row. The implants were designed to act as articulating spacers capable of maintaining the relationship of adjacent carpal bones after excision of the lunate while preserving mobility of the wrist.

An initial attempt to develop a lunate implant resulted in an implant having essentially the same anatomical shape as the bone being replaced. This implant was developed through exhaustive anatomical shaping and sizing of cadaver bones and roentgenographic studies of a variety of hands. The lunate implant was provided in progressive sizes and concavities were more pronounced then the lunate bone replaced in an attempt to increase stability. A stabilizing stem was formed integral with the implant and fitted into the intramedullary canal of the triquetrum bone.

A second form of lunate implant was developed having a deeper concavity at the distal surface of the implant in an attempt to obtain a better fit around the head of the capitate and therefore obtain increased stability. This increased concavity was not totally satisfactory since impingement with the ligaments of the carpace resulted. Initial silicone implants were essentially anatomically reproduced equivalents to the bones being replaced. These implants included multifaceted and angled and curvilinear surfaces which represented mean averages of approximately 72 different measurements made on each of over one hundred lunate bones. It was believed that an anatomically correct implant including a deeper concavity on the distal surface which articulates with the capitate bone, would result in the most stable arthroplastic reconstruction.

SUMMARY OF THE INVENTION

In accordance with the present invention a lunate implant is provided which results in increased stability and which is not a multifaceted, complexly surfaced implant mimicking the bone replaced. Essentially, the unique lunate implant includes a planar triquetrum face having a generally U-shape in plan and including outwardly angled lateral edges, a curvilinear proximal edge and a curvilinear distal edge having a radius of curvature greater than the radius of curvature of the proximal edge and astabilizing stem extending outwardly from and perpendicular to the planar triquetrum face which is adapted to be inserted within the intramedullary canal of the triquetrum bone. The body further includes a planar scaphoid face having a configuration similar to the planar triquetrum face but having an overall length less than the length of the triquetrum face. The scaphoid face is adapted to articulate with the scaphoid bone and defines with the triquetrum face an included, acute angle from the distal to the proximal edges. A cupped, concave, smooth distal surface is adapted to articulate with the head of the capitate bone to stabilize the implant. The distal surface is less pronouncely cupped than with the prior lunate implants and includes lateral edges defined by the distal edges of the triquetrum and scaphoid faces. A proximal surface has a smooth convex shape and joins the proximal edges of the triquetrum and the scaphoid faces. The proximal surface has a decreasing or double radius between the triquetrum and the scaphoid faces.

Generally planar, dorsal and palmar surfaces extend between the dorsal lateral edges of the triquetrum and scaphoid faces and the palmar lateral edges of the triquetrum and scaphoid faces, respectively. Both the dorsal and palmar surfaces have straight distal edges and curved proximal edges smoothly joining with the proximal surface of the body. The body of the implant is substantially symmetrical about a longitudinal centerline passing through the distal and proximal surfaces and along the longitudinal centerlines of the scaphoid and triquetrum faces.

DETAILED DESCRIPTION OF THE PREFERRED EMBODIMENT

Figure 1:
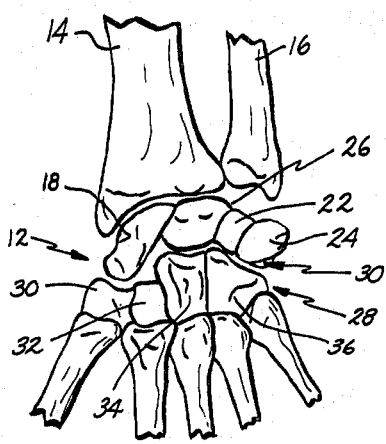
FIG. 1 is a fragmentary, anterior view of a wrist joint showing the distal and proximal carpal rows.

With reference to the drawings, FIG. 1 illustrates an anterior view of a wrist. The bones that make up the wrist joint include a proximal carpal row 12. The proximal carpal row is adjacent the radius 14 and the ulnar 16 of the arm and includes a scaphoid bone 18 and a lunate bone 26, a triquetrum bone 22 and the pisiform bone 24. The joint of the wrist extending along the proximal carpal row of the wrist between the distal radius is referred to as the radiocarpal joint. The wrist joint further includes a distal carpal row 28. The distal carpal row includes a trapezium bone 30, a trapezoid bone 32, a capitate bone 34 and a hamate bone 36. A midcarpal joint 38 of the wrist extends between the distal and proximal carpal rows.

Wrist movement is divided between the radiocarpal and midcarpal joints of the wrist in a relatively complex manner. Displacement of the carpal bones is necessary for bone motion. The configurations of each row of bones changes according to the position of the hand. Flexion and extension movements are fairly equally divided between the proximal and distal rows of carpal bones while ulnar and radial deviation movements occur mostly at the radiocarpal joint. Anatomical distortion of the carpal bones or loss of integrity of their ligaments or secondary stiffness affects the joints and results in wrist disability.

The carpal bones are held together by short interosseous ligaments. Ulnar collateral and radial collateral ligaments provide lateral support of the wrist. Palmar radiocarpal and dorsal radiocarpal ligaments maintain support of the carpal area. The fibers of the palmar radiocarpal ligament extend distally and obliquely from the radius, the triangular fibrocartilage and styloid process of the ulna. These ligaments define a symmetrical pattern due to insertions into the scaphoid, lunate, triquetrum and capitate bones. It is important that the integrity of the radiocarpal and ulnocarpal bands of ligaments be maintained in carpal bone surgery and that these ligaments not be interferred with or impinged on by the implant.

The lunate bone 26 articulates proximally about the radius, distally about the capitate and hamate bones, laterally about the scaphoid bone and medially about the triquetrum bone. The lunate bone has a deeply concave and crescent outline and is situated in the center of the proximal row of the carpus. The bone distal surface is deeply concave and articulates with the head of the capitate by a long narrow facet separated by a ridge from the general surface of the hamate bone. The dorsal and palmar surfaces are rough and serve as points for attachment of the ligaments. The lateral surface includes a narrow, flat, semilunar facet for articulation with the scaphoid and the medial surface includes a smooth, quadrilateral facet for articulation with the triquetrum.

Initial attempts to provide a lunate implant involved detailed empirical studies of an excess of 100 lunate bones and resulted in a series of graduated implants which were anatomically very similar to the bone replaced. While being successfully employed in arthroplastic reconstruction of the wrist joint, the stability obtained did not as closely approach that normally present in a non-defective wrist joint as was desired. In an attempt to obtain a more stable implant, the distal surface, which articulates around the capitate, was more deeply cupped. Although increasing the stability of the implant at the capitate head, this deeper cupping resulted in impingement on the ligaments and therefore did not provide a completely satisfactory solution to the problems encountered.

Figure 2:
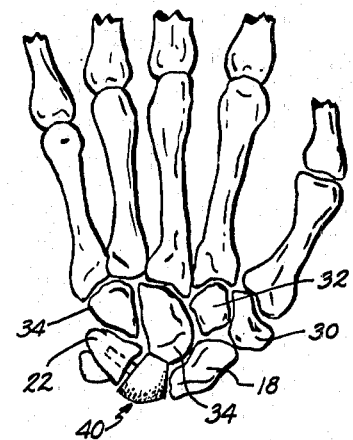
FIG. 2 is a posterior view of a wrist joint showing a lunate implant in accordance with the present invention.

As illustrated in FIG. 2 and explained in detail below, the present invention provides a lunate implant generally designated 40, which is surgically positioned to articulate with the capitate bone 34, the triquetrum bone 22, the scaphoid bone 18 and the radius 14.

As seen in FIGS. 3–6, the lunate implant 40 includes a posterior or dorsal surface 42, a triquetrum face or medial surface 44, a scaphoid face or lateral surface 46, a proximal surface 48, a distal surface 50 and an anterior or palmar surface 51. Extending outwardly from and perpendicular to the triquetrum or medial surface 44 is a stabilizing stem 52. The scaphoid face 46 and the triquetrum face 44 are flat or planar and are angularly related. The surfaces 44, 46 opening from the distal surface 50 to the proximal surface 48 define an acute included angle designated a. The surfaces 44, 46, are adapted to abut against and articulate with the triquetrum and the scaphoid bones, respectively. The flat or planar surfaces, it is believed, result in an unexpected increase in the stability of the implant when compared with prior implants.

Figure 7:
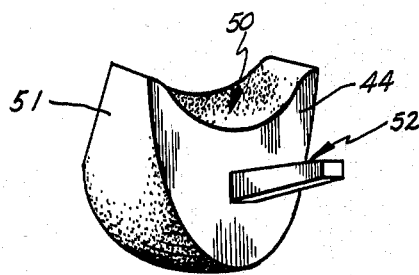
FIG. 7 is a perspective view showing the triquetrum or medial surface of the implant.
Figure 8:
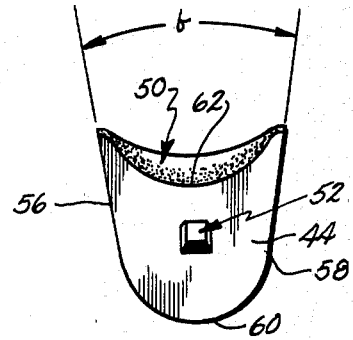
FIG. 8 is an elevational view of the triquetrum surface of the implant.

As seen in FIGS. 7 and 8, the triquetrum surface 44 has a general U-shape in plan and includes outwardly angled edges 56, 58. The edges 56, 58 define an included angle extending outwardly from a proximal edge 60 of the face to a distal edge 62 which is designated b. The proximal edge 60 of the face 44 is curved and has a radius of curvature less than the radius of curvature of the distal, curved edge 62. The stabilizing stem 52 extends outwardly from the face 44 generally perpendicular thereto and is in the shape of a truncated, tapered rectangle. The stem extends outwardly offset along the vertical centerline of the face 44, as seen in FIG. 8, towards the distal edge 62. The stem 52 is dimensioned and adapted to be inserted within the intramedullary canal of the triquetrum bone. It is presently preferred that the stem 52 be positioned on the triquetrum face since the interface between the triquetrum and the lunate has the least amount of movement in the carpal row.

Figure 4:
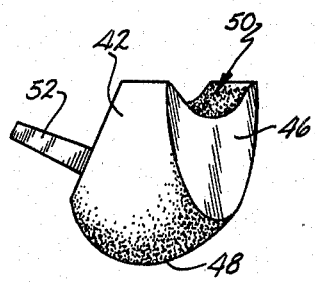
FIG. 4 is a perspective view of the scaphoid or lateral surface of the implant.
Figure 5:
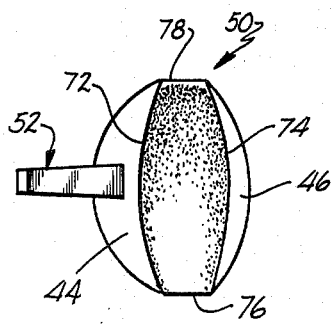
FIG. 5 is a plan view illustrating the distal surface of the implant.
Figure 9:
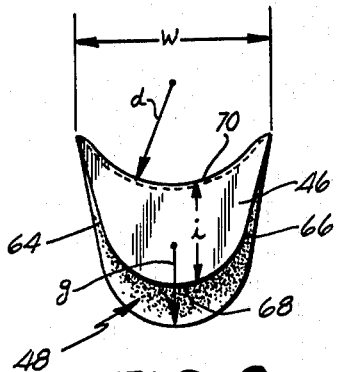
FIG. 9 is an elevational view showing the scaphoid surface of the implant.

As seen in FIGS. 4 and 9, the scaphoid face 46 has the same general configuration as the triquetrum face 44. However, the vertical height or longitudinal dimension of the face 46 is less than that of the face 44. The face 46 is similarly flat or planar, has a general U-shape in plan and includes lateral edges 64, 66 which extend outwardly from a proximal edge 68 to a distal edge 70. The distal edge 70 is curvilinear and has a radius of curvature greater than the curvilinear proximal edge 68. The edges 64, 66 lie in substantially the same perpendicular plane as the lateral edges 56, 58 of the triquetrum face. The scaphoid face 46 is adapted to abut and articulate with the scaphoid bone 18 as shown in FIG. 2.

As seen in FIGS. 4, 5, 6 and 7, the distal surface 50 of the implant 40 is concave and smoothly cupped in shape. The surface 50 is adapted to engage the head of the capitate bone 34 to stabilize the implant. The surface 50 has a sufficient concavity so as to provide stability but is not so deep as to impinge upon ligaments. The surface 50 includes a transverse curvature having a radius designated c and a longitudinal curvature having a radius designated d. The concavity defined by the surface 50 is substantially less than that provided by prior lunate implants. The lateral edges 72, 74 of the distal surface 50 are curvilinear in shape and are defined by the distal edges 62, 70 of the triquetrum face 44 and the scaphoid face 46, respectively. The posterior or dorsal edge and the anterior or palmar edge 76, 78 of the dorsal surface 50 are substantially straight edges.

Figure 3:
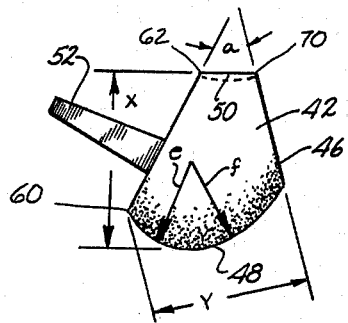
FIG. 3 is an elevational view showing the posterior or dorsal surface of the implant.

As seen in FIGS. 3 and 4, the dorsal surface 42 of the implant is generally planar and joins the dorsal edges of the triquetrum surface and the scaphoid surface 46. The surface 42 has the shape of a truncated V in plan and smoothly joins into the proximal surface 48 of the implant.

Figure 6:
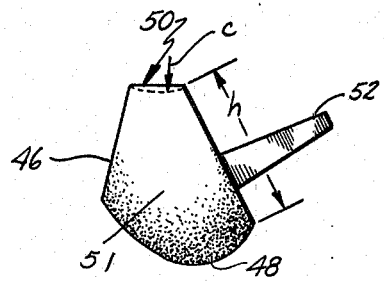
FIG. 6 is an elevational view showing the anterior or palmar surface of the implant.

As seen in FIGS. 6 and 7, the lunate implant body also defines a palmar or anterior surface 51 which is the mirror image of the dorsal surface 42. This surface similarly possesses a generally truncated V-shape in plan, is generally planar or flat, and smoothly joins into the proximal surface 48 of the implant body.

Figure 10:
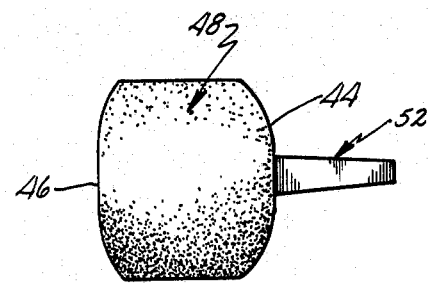
FIG. 10 is a plan view showing the proximal surface of the implant.

As best seen in FIGS. 3, 9 and 10, the proximal surface 48 is smoothly curvilinear in shape and includes a decreasing radius curve defined by two radii from the triquetrum face 44 to the scaphoid face 46. This surface includes a first radius designated e and a second smaller radius designated f. Also, as seen in FIG. 9, this surface is defined by a third, transverse radius designated g, extending between the dorsal and palmar surfaces of the implant body. Radius g is the same as the radius of curvature of the proximal edge 60 of face 44. The proximal surface 48 articulates with the radius bone 14.

In a presently existing embodiment of the lunate implant in accordance with the present invention, the angle a included by the triquetrum face and the scaphoid face is approximately 30°. The angle b included by the lateral edges 56, 58 of the triquetrum face 44 is approximately 28°. The longitudinal distance h from the proximal edge 60 of the triquetrum face 44 to the dorsal edge 62 is approximately 0.4 inches. The distance i from the proximal edge 68 to the dorsal edge 70 along the vertical centerline, as seen in FIG. 9 of the scaphoid face 46, is approximately 0.3 inches. The distance W shown in FIG. 9, which represents the length of the dorsal surface 50, is approximately 0.630 inches. The maximum distance or overall length of the implant (FIG. 3) from the dorsal surface 50 to the highest point on the proximal surface 48 along a single plane is approximately 0.53 inches.

The transverse distance between the proximal edge of the triquetrum face 44 and the proximal edge of the scaphoid 46, designated y in FIG. 3, is approximately 0.52 inches. The stabilizing stem 52 has a length of approximately 0.32 inches and tapers from a square width at its juncture with a triquetrum face of approximately 0.10 inches to a square width of approximately 0.075 inches. The radius d (FIG. 9) is approximately 0.39 inches and the radius c (FIG. 6) is approximately 0.2 inches. The radius f (FIG. 3) is approximately 0.43 inches and the radius g (FIG. 9) is approximately 0.26 inches. A plurality of implants of graduated size are preferably provided to insure a stable fit with the individual patient. Each of these implants are graduated to have the same general proportions as the preferred embodiment illustrated. For example, the ratio of the longitudinal length of the scaphoid face and the triquetrum face is approximately 0.75, the ratio of the transverse radius c to the longitudinal radius d of the distal surface is approximately 0.55. The included angle b would remain at 28° and the included angle a would remain at 30°. The ratio of the overall width w to the overall length x would be approximately 1.29. This ratio may be varied within the range of 1.08 to 1.29 and acceptable results will be obtained. The ratio of radius d to radius g may decrease within the range of 1.48 to 1.2 as the overall length increases from 0.55 inches to 0.73 inches and acceptable results will be obtained.

The implant in accordance with the present invention results in an improved fit and is firmly supported on all sides by adjacent bones. The implant in situ is analogous to a ball bearing in function and must be surrounded by a "housing". Therefore, a tight capsuloligamentous structure must be insured. When used to correct a collapsed deformity of the wrist, instability will continue unless the ligamentous structures are repaired. The stem 52 is included primarily to provide stability during the early postoperative phase.

Insertion of a lunate implant is indicated for avascular necrosis or in the case of longstanding dislocation. The implant should not be employed when the arthritic involvement is not localized in the lunate articulation if complete relief of pain is sought. In the case of longstanding dislocations and advance cases of avascular necrosis, the space for the lunate implant may be substantially reduced in size, resulting in fitting problems. Also, loss of integrity of the capsular structures due to fracture dislocation or collapsed deformity of the wrist may be a contra-indication to the implant procedure unless the carpal bone relationship is reestablished and ligaments are repaired.

A surgical procedure for implantation of the lunate involves either a dorsal, a volar or palmar incision. If a dorsal longitudinal incision is used, the wrist capsule is transversely incised between the third and fourth dorsal compartments and carefully preserved. The extensor pollicis longus tendon is retracted radially and the dissection is carried downward radial to the compartment of the extensor digitorum communis tendons. The capsule is then incised over the lunate and dissected close to the radius of the underlying carpal bones. The lunate bone is removed en bloc or piecemeal. Care must be exercised to avoid injury to the palmar, radiocarpal and ulnocarpal ligaments. The integrity of the interior capsuloligamentous structures is verified and the ligament structures are brought together with sutures to assure a firm, palmar capsulous support. An implant sizing set is then used to determine the correct size of the implant. The implant should be selected so that it will comfortably fit in the space of the resected lunate. A small curet or drill is used to make a hole in the triquetrum to accept the stem of the implant. This hole should not be larger than the stem and minimal trauma to the triquetrum bone should be allowed. The hole should be directed such that the stem placement will orient the implant in accurate anatomical relationship to the contingeous bones.

The dorsal capsule is then tightly sutured by means of an inverted knot technique. A strip of extensor retinaculum can be used to reinforce the dorsal carpal ligaments. The tendon compartments are then brought back into position so that there will be no adherence to the underlying structures. The wound is closed in layers and a small silicone, rubber drain is placed subcutaneously.

The lunate implant in accordance with the present invention is easily and relatively inexpensively manufactured with conventional molding techniques from medical grade silicone rubbers. The implant is employed with a relatively simple surgical procedure that has the potential of permitting wrist motion with increased stability from that heretofore obtained, mobility and freedom from pain. The above description should be considered as that of the preferred embodiment. The true spirit and scope of the present invention may be determined by reference to the appended claims.

The embodiments of the invention in which an exclusive property or privilege is claimed are defined as follows.

1. An implant for replacement of the lunate bone, said implant adapted to be surgically positioned adjacent the triquetrum bone, the scaphoid bone, the capitate bone and the radius bone, said implant comprising:

a one piece body of resilient material, said body defining:

a planar triquetrum face having a general U-shape in plan and including outwardly angled edges, a curvilinear proximal edge and a curvilinear distal edge, said distal edge having a radius of curvature greater than the radius of said proximal edge and a stabilizing stem extending outwardly from and perpendicular to said planar triquetrum face, said stem adapted to be inserted within the intramedullary canal of the triquetrum bone;

a planar scaphoid face having a general U-shape in plan and including outwardly angled edges lying in substantially the same perpendicular plane as the lateral edges of the triquetrum face, said scaphoid face having a curvilinear proximal edge and a curvilinear distal edge, the radius of curvature of the distal edge being substantially the same as the radius of curvature of the distal edge of said triquetrum face, said scaphoid face having a length less than the length of said triquetrum face and being adapted to articulate with the scaphoid bone, said scaphoid face and said triquetrum face being angled outwardly with respect to each other from said distal edges to said proximal edges;

a cupped, concave, smooth distal surface adapted to articulate with the head of the capitate bone to stabilize said implant, said distal surface lateral edges being defined by said distal edges of said triquetrum and said scaphoid faces;

a proximal surface having a smooth convex shape joining said proximal edges of said triquetrum and said scaphoid faces;

a generally planar dorsal surface extending between the dorsal lateral edges of said triquetrum and scaphoid faces, said dorsal surface having a straight distal edge and a curved proximal edge smoothly joining with said proximal surface, said proximal edge having a decreasing radius from said scaphoid face to said triquetrum face; and a generally planar palmar surface extending between the palmar lateral edges of said triquetrum and scaphoid faces, said palmar surface having a straight distal edge and a curved proximal edge smoothly joining with said proximal surface, said body being substantially symmetrical about a longitudinal centerline passing through said distal surface and said proximal surface and along the longitudinal centerlines of said scaphoid and said triquetrum faces.

2. An implant as defined by claim 1 wherein the included angle between said scaphoid and said triquetrum faces if approximately 30°.

3. An implant as defined by claim 2 wherein the edges of said triquetrum face are angled outwardly from each other at an angle of approximately 28°.

4. An implant as defined by claim 3 wherein the ratio of the radius of curvature of the distal edge of said triquetrum face to the proximal edge of said triquetrum face is in the range of 1.2 to 1.48.

5. An implant as defined by claim 4 wherein the ratio of the length of the centerline of said scaphoid face to the centerline of said triquetrum is approximately 0.75.

6. An implant as defined by claim 5 wherein the ratio of the overall width of the body to the overall length of the body is in the range of 1.08 to 1.29.

7. An implant as defined by claim 6 wherein the distal surface has a transverse radius and a longitudinal radius of the ratio of the transverse radius to the longitudinal radius is approximately 0.55.

* * * * *

UNITED STATES PATENT AND TRADEMARK OFFICE
CERTIFICATE OF CORRECTION

PATENT NO. : 4,164,793
DATED : August 21, 1979
INVENTOR(S) : Alfred B. Swanson

It is certified that error appears in the above-identified patent and that said Letters Patent are hereby corrected as shown below:

Column 2, line 20:

"astabilizing" should be --a stabilizing--

Column 8, Claim 2, line 26:

"if" should be --is--.

Signed and Sealed this

Twelfth Day of February 1980

[SEAL]

Attest:

SIDNEY A. DIAMOND

*Attesting Officer*   *Commissioner of Patents and Trademarks*